US007166072B2

(12) United States Patent
Smith

(10) Patent No.: US 7,166,072 B2
(45) Date of Patent: Jan. 23, 2007

(54) SEXUAL THERAPY DEVICE

(76) Inventor: Irina Smith, 88 E. Broad St., Suite 1220, Chicago, IL (US) 43215

( * ) Notice: Subject to any disclaimer, the term of this patent is extended or adjusted under 35 U.S.C. 154(b) by 210 days.

(21) Appl. No.: 10/710,926

(22) Filed: Aug. 12, 2004

(65) Prior Publication Data

US 2006/0074273 A1 Apr. 6, 2006

Related U.S. Application Data

(60) Provisional application No. 60/521,954, filed on Jul. 26, 2004.

(51) Int. Cl.
*A61F 5/00* (2006.01)

(52) U.S. Cl. ........................................................ 600/38

(58) Field of Classification Search ............... D24/214, D24/211, 215; 601/46, 67, 78, 80, 82, 83, 601/84, 85, 89, 97, 68; 600/38–41
See application file for complete search history.

(56) References Cited

U.S. PATENT DOCUMENTS 4,190,042 A * 2/1980 Sinnreich .................... 600/204
5,067,480 A 11/1991 Woog et al.
5,080,088 A * 1/1992 LeVahn ...................... 600/206
D339,198 S * 9/1993 Mochida .................... D24/214
5,308,327 A * 5/1994 Heaven et al. ......... 604/103.09
D359,563 S * 6/1995 Chi ........................... D24/214
5,470,303 A * 11/1995 Leonard et al. ............... 601/84
5,895,352 A * 4/1999 Kleiner ....................... 600/206
6,656,139 B2 * 12/2003 Zwezdaryk .................. 601/46
6,749,557 B2 * 6/2004 Garland ....................... 600/38
2002/0188234 A1 * 12/2002 Manska ....................... 601/70

OTHER PUBLICATIONS

Adam & Eve Catalog Dec. 2002, Cover and pp. 2,3, 46, 47.*

* cited by examiner

*Primary Examiner*—Samuel G. Gilbert
(74) *Attorney, Agent, or Firm*—Jeffrey Furr

(57) ABSTRACT

The current invention consists of a device for sexual therapy that consists of a handle connected to a long tear shaped flat surface which curves downward at the largest end of the tear. On the flat inward side of the downward part of the tear there is a raised platform which is covered by pimples. The end of the handle has a flat edge which serves as a cap for a battery compartment with the cap having an on/off/speed control switch. The pimples of the raised platform are used for sexual stimulation. Within the device under the platform is a vibrating means such as a vibrating bullet.

8 Claims, 6 Drawing Sheets

SEXUAL THERAPY DEVICE

CROSS REFERENCE TO RELATED APPLICATIONS

This is a non-provisional of provisional application 60/521,954 filed on Jul. 26, 2004.

BACKGROUND OF INVENTION

This invention relates to a stimulator or marital aid for use in marital/sexual therapy.

Background

Within the last several decades, the existence and desirability of the female orgasm has been virtually universally accepted by civilized society. It is well-established that a large percentage of women do not orgasm regularly during sexual intercourse, but that female orgasm is desirable. The lack of female orgasm, for a substantial number of couples, can lead to tension and frustration which, in turn, leads to marital discord.

Orgasmic therapy for women usually involves self-stimulation. While there are internal (vaginal) orgasms which are by some considered a more mature form of orgasm than external (clitoral) orgasms or merely the result of indirect external pressure, it is much easier for the woman to self-stimulate external orgasms and therefore external pressure is usually the method of choice in orgasmic therapy. The vulva surrounds the opening of the vagina, the musculomembranous tubular structure extending from the vulva to the uterine cervix. The vulva includes the clitoris, a highly sensitive sex organ which, when stimulated appropriately, provides sexual satisfaction. The clitoris, homologous to the penis, is a small cylindrical organ situated at the anterior part of the vulva.

Many women are reluctant to stimulate themselves manually so a mechanical device such as a vibrator may be required for effective marital therapy. The couple can use the vibrator or marital aid on a maintenance or recreational program. A vibrator can also be used in the context of a married couple where the wife simply has a greater sexual appetite or is slower to respond and climax than is the husband.

Additionally, it is well-established that the female orgasm relieves cramps during menstruation but many couples are reluctant to engage in sexual activity during menstruation. At these times a vibrator can be used for the relief of cramps and irritability associated with menstruation.

A vibrator can be used to assist the disabled or elderly to induce orgasms after the death, desertion or lack of capacity or availability of a spouse. A vibrator can assist woman having organisms while her husband is injured, ill or absent for long periods.

In the past, vibrators were frequently phallic-shaped to simulate the movement of the husband's sexual organ. This kind of vibrator is possibly the result of male misunderstanding of the process of the female orgasm since direct clitoral pressure is the method of choice for marital orgasmic therapy. Similarly, vibrators of the prior art are sometimes large, heavy and cumbersome to use.

There is still room for improvement in the art.

SUMMARY OF INVENTION

The current invention consists of a device for sexual therapy that consists of a handle connected to a long tear shaped flat surface which curves downward at the largest end of the tear. On the flat inward side of the downward part of the tear there is a raised platform which is covered by pimples. The end of the handle has a flat edge which serves as a cap for a battery compartment with the cap having an on/off/multiple speed control switch. The pimples of the raised platform are used for sexual stimulation. Within the device under the platform is a vibrating means such as a vibrating bullet. The flat design and soft exterior casing provides a cushion between the bodies of two partners and is designed so that pressure from the partners bodies secures the device during sexual activity while nevertheless remaining comfortable, yet curved to conform to the contours of a woman's body It is therefore an object of this invention to provide a stimulator or marital aid for direct external stimulation for marital/sexual orgasmic therapy.

It is therefore a further object of this invention to provide a stimulator or marital aid which is gentle and adapted to apply stimulation over an appropriate area for marital/sexual orgasmic therapy.

It is therefore a still further object of this invention to provide a stimulator which is designed at a suitable angle following the natural female body curve for use in marital/sexual orgasmic therapy.

It is therefore a still further object of this invention to provide a stimulator which is light easy to hold and quiet.

BRIEF DESCRIPTION OF DRAWINGS

Without restricting the full scope of this invention, the preferred form of this invention is illustrated in the following drawings.

DETAILED DESCRIPTION

Figure 1:
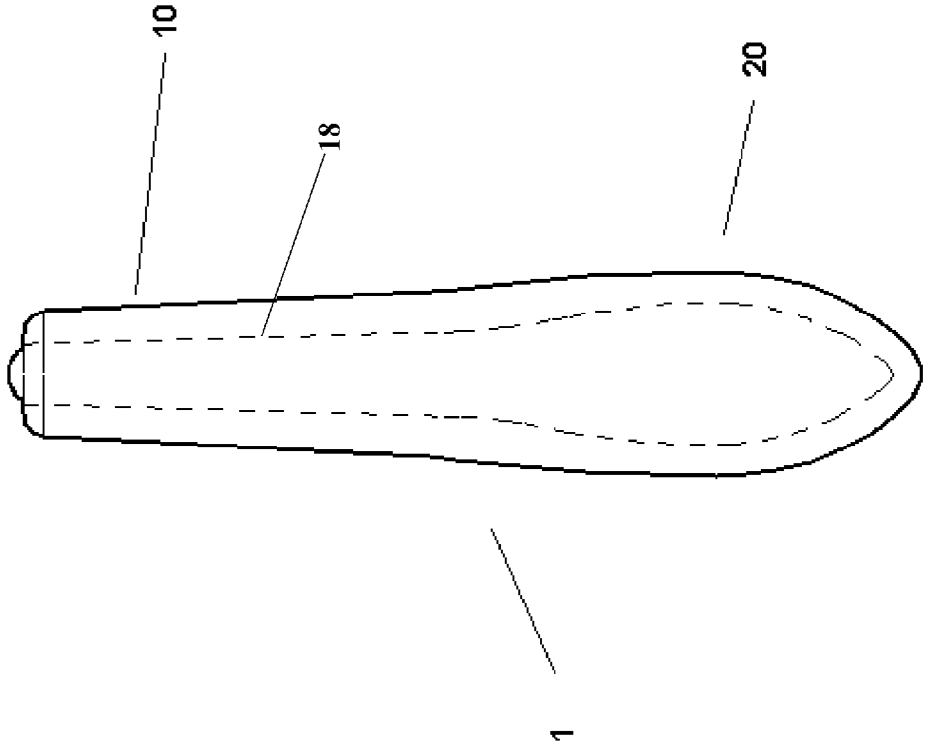
FIG. 1 shows a top view of the device.

The following description is demonstrative in nature and is not intended to limit the scope of the invention or its application of uses.

There are a number of significant design features and improvements incorporated within the invention.

As shown in FIGS. 1, 2, 3, 4, 5 and 6, the current invention is a device 1 for sexual therapy and stimulation.

The vulva surrounds the opening of the vagina, the musculomembranous tubular structure extending from the vulva to the uterine cervix. The vulva includes the clitoris, a highly sensitive sex organ which, when stimulated appropriately, provides sexual satisfaction. The clitoris, homologous to the penis, is a small cylindrical organ situated at the anterior part of the vulva.

During sexual intercourse, the penis is reciprocally and slidingly received in the vagina. The penis typically does not make substantial contact with the clitoris. Rather, the abdomen and the transition area from which the base of the penis extends provides the critical contact that may ultimately lead to sexual satisfaction. Sexual satisfaction in females generally is not derived from linear translation of the penis through the vagina, rather rhythmic pressure against and/or frictional engagement with the clitoris.

The device 1 consists of a handle 10 that is connected to a tear base 20 which is a long tear shaped flat surface which curves downward at the largest end of the tear 20 where the point is. The handle is made of a smooth plastic while the rest of the device 1 including the tears 20 is made of a soft rubber material in the preferred embodiment.

Figure 2:
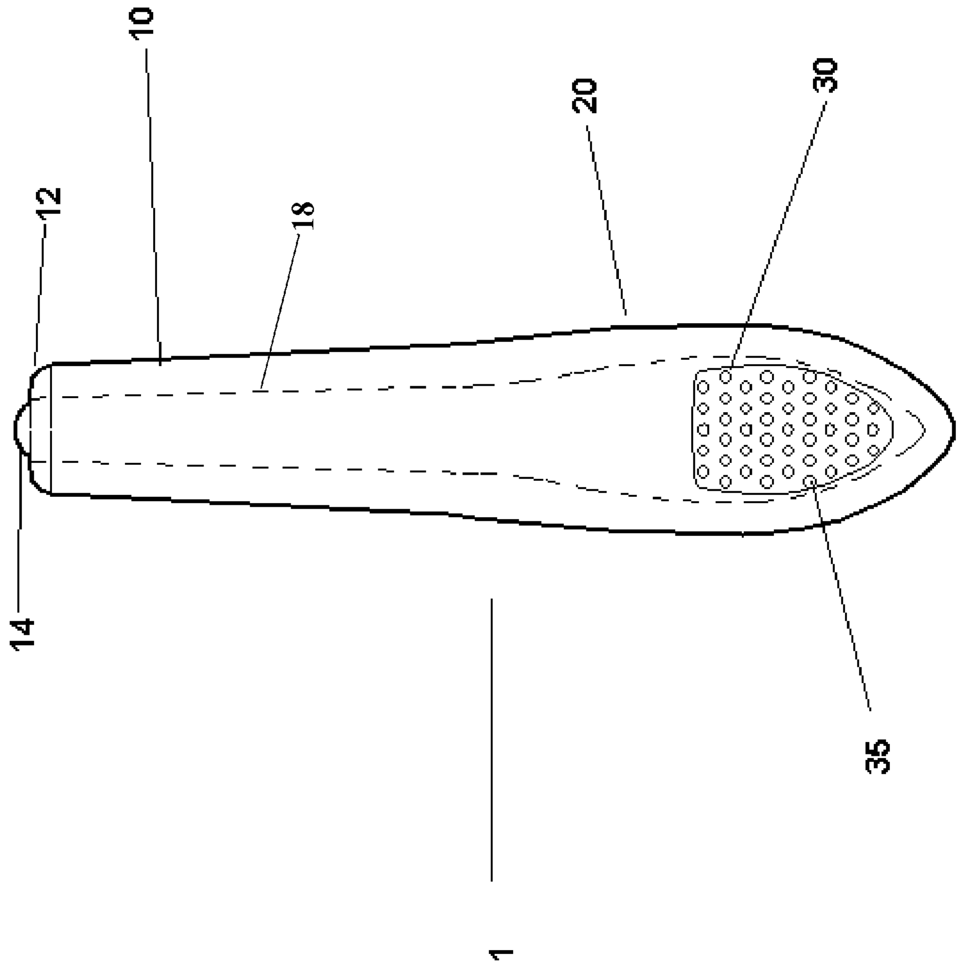
FIG. 2 shows a bottom view of the device.
Figure 3:
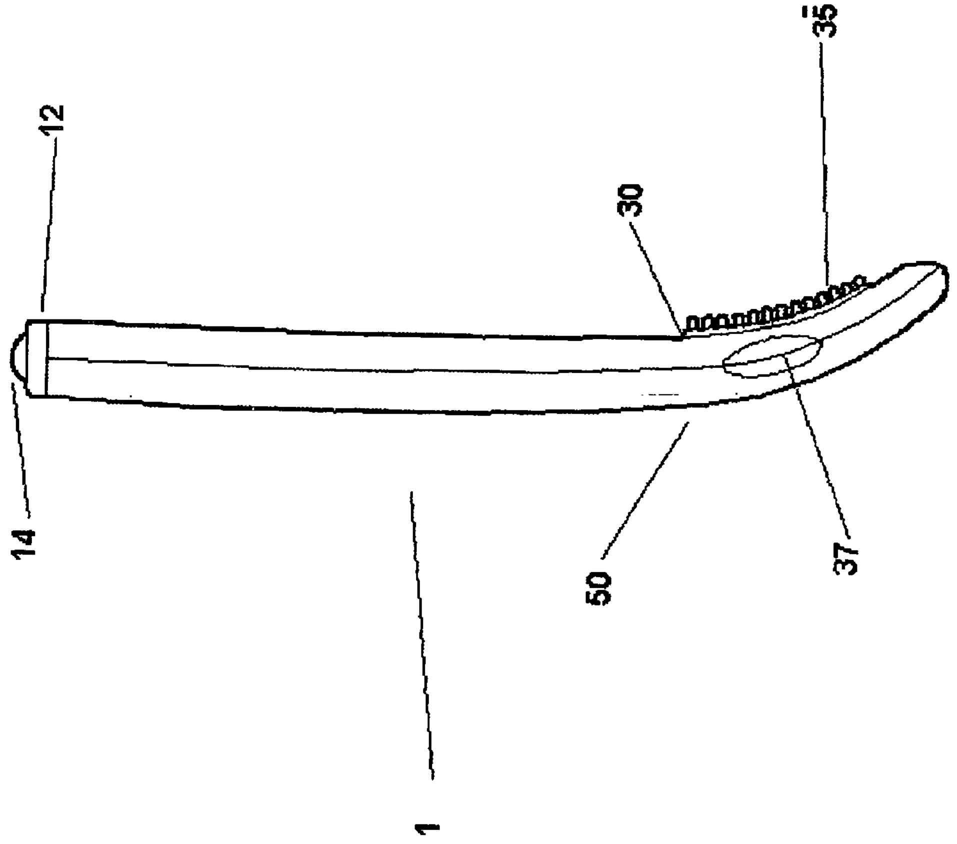
FIG. 3 displays a side view of the device.
Figure 4:
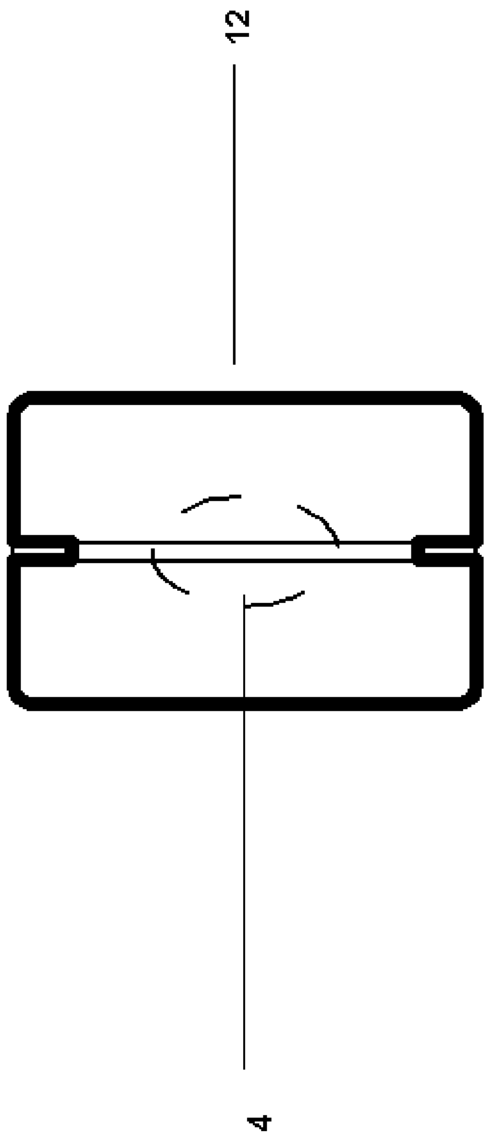
FIG. 4 displays the cap of the device.
Figure 5:
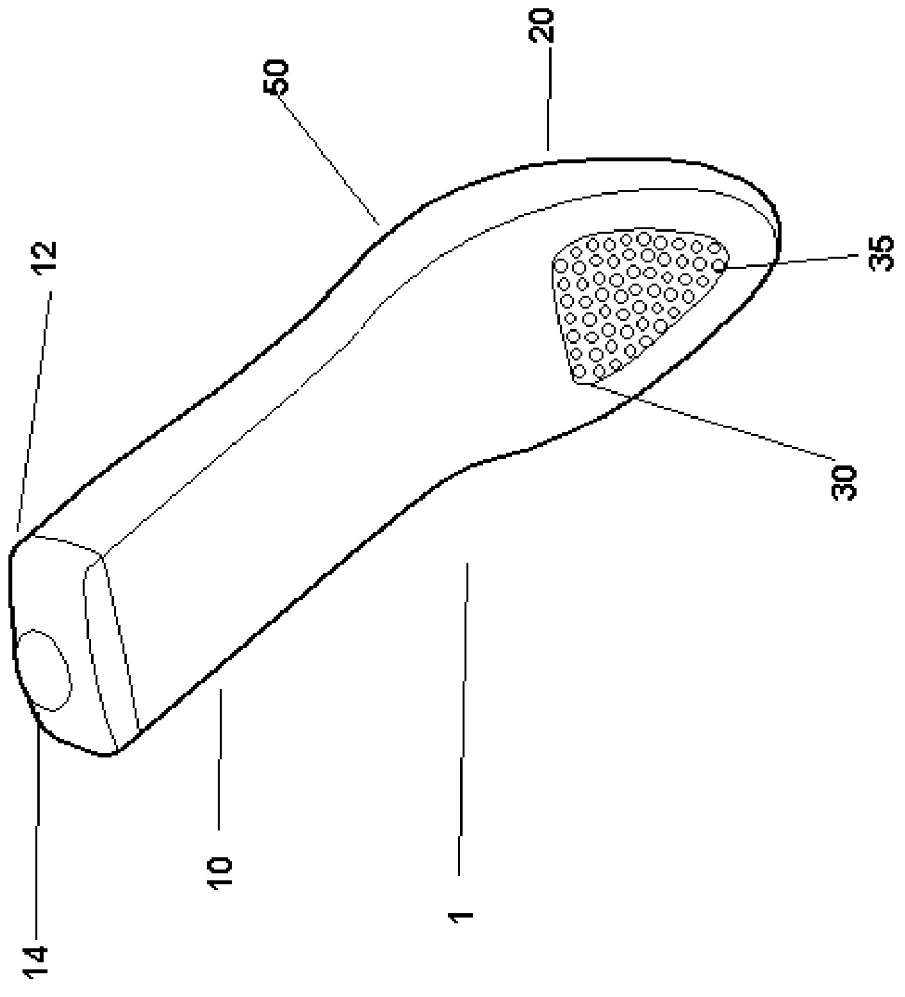
FIG. 5 shows an elevated front view of the device.

As shown in FIGS. 2, 3 and 4, on the flat inward side of the downward part of the tear 20 there is a raised platform 30 which is covered by pimples 35. It is these pimples 35 that are used for the external stimulation of the sex organs such as the clitoris and vulva. Within the device under the platform 30 is a vibrating means 37. In the preferred embodiment a vibrating bullet is used as a vibrating means 37. The vibrating means 37 transfers the vibrations to the platform 30 which transfers the vibrations to the pimples 35. This gives a vibration motion to the pimples 35 that produces the best motion for sexual stimulation without being too hard, avoiding tissue damage and/or pain.

Figure 6:
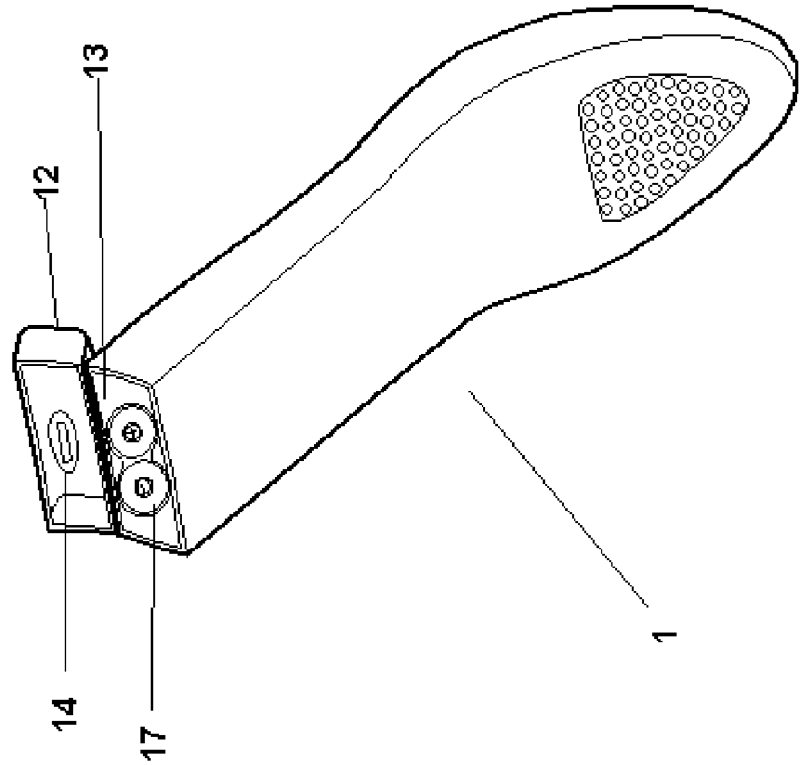
FIG. 6 shows an elevated front view with the cap open.

As shown in FIG. 6, the handle 10 has a flat edge which serves as a cap 12 for a battery compartment 13. The cap has an on/off/multiple speed control switch 14. In the preferred embodiment, this switch 14 is a slide switch which can be used to turn the device 1 on and off and switch to multiple vibration speeds. The handle 10 has a smooth texture. The tear shaped 20 part of the device is encased with a soft rubber coating making it water proof, adding to the vibrationary motion and giving it the proper texture for sexual stimulation.

At the end of the handle 10 of the device 1, there is a hinged cap 12 that opens through a hinging means to allow the insertion of two AA batteries 17 into the battery compartment 13. The handle 10 will have a closing means such as a latch to keep the cap 12 closed.

The device 1 has a power source 17 which is two double A batteries in the preferred embodiment. The power source 17 is connected to the control switch 14 and the vibrating means 37 through the use of standard wires. The control switch 14 is a slide control switch with on, off, low, medium and high positions. The device 1 is design for quiet operation. The quiet operation is an important aspect as so the user is not distracted.

The curve 50 of the device 1 is designed to match the contour of a woman's body so that it is easy to use while placing the raised platform 30 on the external sex organs.

This makes the device 1 easier to use either by herself or for use by her partner. This curve 50 is very important to the design of the device 1. The curve 50 is held by a shape holder 18. The shape holder 18 is a metal piece that holds the shape of the device. It is sufficiently rigid to hold the shape of the device 1, because of the soft nature of the materials used.

The flat design and soft exterior casing of the device 1 provides a cushion between the bodies of two partners and is designed so that pressure from the partners bodies secures the device 1 during sexual activity while nevertheless remaining comfortable, yet curved to conform to the contours of a woman's body.

ALTERNATIVE EMBODIMENT

The connection of the handle 10 to the tear shaped body 20 can be designed to be flexible with some give. This will make the device 1 easier to use as it will not exert too much pressure on the external sexual organs deceasing the potential for the device 1 to be held too hard to the external sexual organs.

CONCLUSION

The device is a great stimulator or marital aid for direct external stimulation for marital/sexual orgasmic therapy.

Although the present invention has been described in considerable detail with reference to certain preferred versions thereof, other versions are possible. Therefore, the point and scope of the appended claims should not be limited to the description of the preferred versions contained herein.

As to a further discussion of the manner of usage and operation of the present invention, the same should be apparent from the above description. Accordingly, no further discussion relating to the manner of usage and operation will be provided.

With respect to the above description, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A device for sexual therapy comprising:

a handle connected to a long tear shaped flat surface winch curves downward at the largest end of the tear with said inward side of the downward part of the tear having a raised platform and having said platform being covered by pimples, with a shape bolder within the device a hold it shape where said shape bolder is made of a metal.

2. A device according to claim 1 further comprising having a vibrating means.

3. A device according to claim 2 further comprising having said vibrating means transferring the vibrations to the platform which transfers the vibrations to the pimples.

4. A device according to claim 2 further comprising having a power source connected to said vibrating means.

5. A device according to claim 2 further comprising having a switch for turning on said vibrating means.

6. A device according to claim 5 where said switch has an on position, an off position and a plurality of speed positions.

7. A device according to claim 2 where said curve matches the curve of a female body in the front of the pelvic region.

8. A device according to claim 1 where said curve matches the curve of a female body in the front of the pelvic region.

* * * * *